(12) United States Patent
DeLuca et al.

(10) Patent No.: US 8,519,169 B2
(45) Date of Patent: Aug. 27, 2013

(54) CRYSTALLIZATION A 1ALPHA-HYDROXY-20-METHYL-2-METHYLENE-19,24,25,26,27-PENTANOR-VITAMIN D3

(75) Inventors: Hector F. DeLuca, Deerfield, WI (US); Agnieszka Glebocka, Madison, WI (US); James B. Thoden, Madison, WI (US); Hazel M. Holden, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/588,608

(22) Filed: Aug. 17, 2012

(65) Prior Publication Data

US 2013/0053587 A1    Feb. 28, 2013

Related U.S. Application Data

(60) Provisional application No. 61/529,007, filed on Aug. 30, 2011.

(51) Int. Cl.
*C07C 401/00* (2006.01)
*A61K 31/59* (2006.01)

(52) U.S. Cl.
USPC .......................................... 552/653; 514/167

(58) Field of Classification Search
USPC .......................................... 552/653; 514/167
See application file for complete search history.

(56) References Cited

U.S. PATENT DOCUMENTS

| 5,086,191 | A | 2/1992 | DeLuca et al. |
| 5,536,713 | A | 7/1996 | DeLuca et al. |
| 5,843,928 | A | 12/1998 | DeLuca et al. |
| 7,943,601 | B2 * | 5/2011 | DeLuca et al. ................ 514/167 |
| 2009/0170822 | A1 | 7/2009 | DeLuca et al. |

FOREIGN PATENT DOCUMENTS

WO    2009086640    7/2009

OTHER PUBLICATIONS

Andrews et al., "A Direct, Regio- and Stereoselective 1Alpha-Hydroxylation of (5E)-Calciferol Derivatives", Journal of Organic Chemistry, 1986, 51: 1635-1637.
Calverley et al., "A Biologically Active Vitamin D Metabolite Analogue", Tetrahedron, 1987, 43(20): 4609-4619.
Choudhry et al., "Synthesis of a Biologically Active Vitamin-D2 Metabolite", Journal of Organic Chemistry, 1993, 58:1496-1500.
Nerinckx et al., "An Improved Synthesis of 1Alpha-Hydroxy Vitamin D3", Tetrahedron, 1991, 47(45): 9419-9430.
Vanmaele et al., "An Efficient Synthesis of 1Alpha-25-Dihydroxy Vitamin D3", Tetrahedron, 1985, 41(1): 141-144.

(Continued)

*Primary Examiner* — Sabiha N Qazi
(74) *Attorney, Agent, or Firm* — Andrus, Sceales, Starke & Sawall, LLP

(57) ABSTRACT

A method of purifying 1α-hydroxy-20-methyl-2-methylene-19,24,25,26,27-pentanorvitamin $D_3$ to obtain 1α-hydroxy-20-methyl-2-methylene-19,24,25,26,27-pentanorvitamin $D_3$ in crystalline form. The method includes the steps of preparing a solvent of either ethyl formate or a mixture of ethyl formate and hexane, dissolving a product containing 1α-hydroxy-20-methyl-2-methylene-19,24,25,26,27-pentanorvitamin $D_3$ to be purified in the solvent, cooling the solvent and dissolved product below ambient temperature for a sufficient amount of time to form a precipitate of 1α-hydroxy-20-methyl-2-methylene-19,24,25,26,27-pentanorvitamin $D_3$ crystals, and recovering the 1α-hydroxy-20-methyl-2-methylene-19,24,25,26,27-pentanorvitamin $D_3$ crystals.

16 Claims, 1 Drawing Sheet

(56) References Cited

OTHER PUBLICATIONS

Vanmaele et al., "1Alpha-Hydroxy Previtamin D3 and its Selective Formation From 1-Keto Previtamin D3", Tetrahedron, 1984, 40(7): 1179-1182.

Vanmaele et al., "A Stereocontrolled Partial Synthesis of 1Alpha-Hydroxy Vitamin D3", Tetrahedron Letters, 1982, 23 (9): 995-998.

Paaren et al., "Direct C(1) Hydroxylation of Vitamin D3 and Related Compounds", Journal of Organic Chemistry, 1980, 45: 3253-3258.

Paaren et al., "Direct C(1) Hydroxylation of Vitamin D Compounds: Convenient Preparation of 1Alpha-Hydroxyvitamin D3, aAlpha,25-Dihydroxyvitamin D3, and 1Alpha-Hydroxyvitamin D2", Proc. Natl. Acad. Sci. USA, 1978, 75(5): 2080-2081.

Sheldrick, "Phase Annealing in SHELX-90: Direct Methods for Larger Structures", Acta Cryst., 1990, A46: 467-473.

Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.

Lythgoe et al., "Calciferol and its Relatives. Part 22. A Direct Total Synthesis of Vitamin D2 and Vitamin D3", J. Chem. Soc. Perkin I, 1978, 590-595.

Lythgoe, "Synthetic Approaches to Vitamin D and its Relatives", Chem. Soc. Rev., 1983, 9: 449-475.

Perlman et al., "Novel Synthesis of 19-Nor-Vitamin D Compounds", Tetrahedron Letters, 1991, 32: 7663-7666.

Sardina et al., "Studies on the Synthesis of Side-Chain Hydroxylated Metabolites of Vitamin D. 2. Stereocontrolled Synthesis of 25-Hydroxyvitamin D2", Journal of Organic Chemistry, 1986, 51: 1264-1269.

Sicinski et al., "New 1alpha,25-Dihydroxy-19-norvitannin D3 Compounds of High Biological Activity: Synthesis and Biological Evaluation of 2-Hydroxymethyl, 2-Methyl, and 2-Methylene Analogs", J. Med. Chem., 1998, 41: 4662-4674.

Toh et al., "Studies on a Convergent Route to Side-Chain Analogues of Vitamin D:25-Hydroxy-23-oxavitamin D3", Journal of Organic Chemistry, 1983, 48: 1414-1417.

Byrn et al., "Pharmaceutical Solids: A Strategic Approach to Regulatory Considerations", Pharmaceutical Research, 1995, 12: 945-954.

International Search Report and Written Opinion, PCT International Application No. PCT/US2012/051384, mailed Aug. 17, 2012.

* cited by examiner

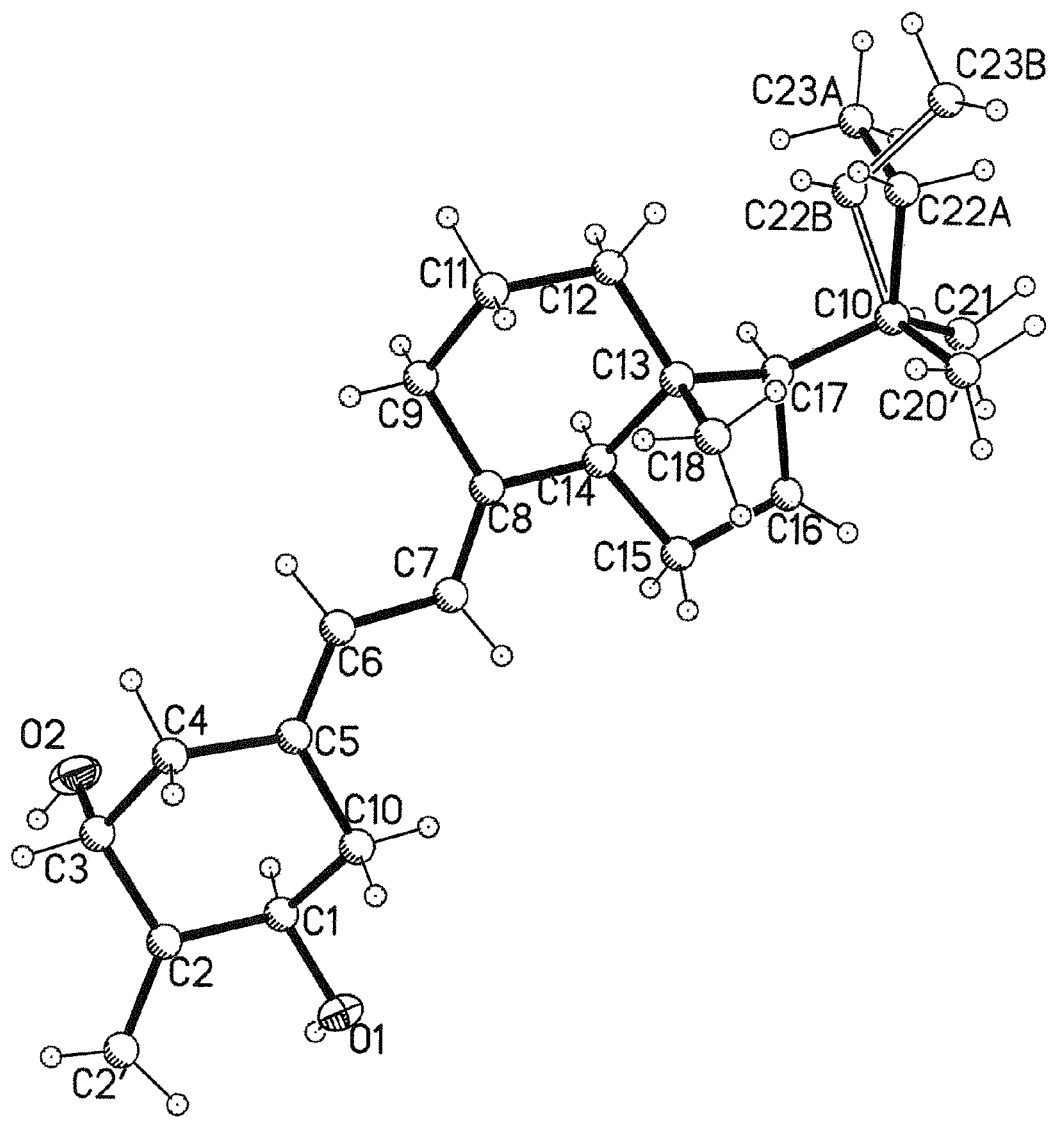

CRYSTALLIZATION A 1ALPHA-HYDROXY-20-METHYL-2-METHYLENE-19,24,25,26,27-PENTANORVITAMIN D3

CROSS REFERENCE TO RELATED APPLICATIONS

This application claims the benefit of U.S. Provisional Application No. 61/529,007, filed Aug. 30, 2011, which is incorporated by reference herein in its entirety for any purpose.

STATEMENT REGARDING FEDERALLY SPONSORED RESEARCH OR DEVELOPMENT

This invention was made with government support under DK047814 awarded by the National Institutes of Health. The government has certain rights in the invention.

BACKGROUND OF THE INVENTION

The present invention relates to purification of organic compounds, and more particularly to the purification of 1α-hydroxy-20-methyl-2-methylene-19,24,25,26,27-pentanorvitamin $D_3$ (referred to herein as "20DCM") by preparing it in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of 5,6-trans geometric isomer of vitamin D is performed, followed by $SeO_2/NMO$ oxidation and photochemical irradiation [see Andrews et al., *J. Org. Chem.* 51, 1635 (1986); Calverley et al., *Tetrahedron* 43, 4609 (1987); Choudry et al, *J. Org. Chem.* 58, 1496 (1993)], the final 1α-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the previtamin D compound, followed by cycloreversion of the modified adduct under basic conditions [Nevinckx et al., *Tetrahedron* 47, 9419 (1991); Vanmaele et al, *Tetrahedron* 41, 141 (1985) and 40, 1179 (1994); Vanmaele et al., *Tetrahedron Lett.* 23. 995 (1982)], one can expect that the desired 1α-hydroxyvitamin can be contaminated with the previtamin 5(10), 6,8-triene and 1β-hydroxy isomer. One of the most useful C-1 hydroxylation methods, of very broad scope and numerous applications, is the experimentally simple procedure elaborated by Paaren et al. [see *J. Org. Chem.* 45, 3253 (1980) and *Proc. Natl. Acad. Sci U.S.A.* 75, 2080 (1978)]. This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path it is reasonable to assume that the final product can be contaminated with 1α-hydroxy epimer, 5,6-trans isomer and the previtamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 0.1-0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of some water-elimination reactions; their driving force is allylic (1α-) and homoallylic (3β-) position of the hydroxy groups. The presence of such above-mentioned oxidation and elimination products can be easily detected by thin-layer chromatography.

Usually, all 1α-hydroxylatation procedures require at least one chromatographic purification. However, even chromatographically purified 1α-hydroxyvitamin D compounds, although showing consistent spectroscopic data, suggesting homogeneity, do not meet the purity criteria required for therapeutic agents that can be orally, parenterally or transdermally administered. Therefore, it was evident that a suitable method of purification of the 1α-hydroxylated vitamin D compound 20DCM is required.

SUMMARY OF THE INVENTION

The present invention relates to a method of purifying 20DCM by means of crystallization to obtain 20DCM in crystalline form. The solvent plays a crucial role in the crystallization process, and is typically an individual liquid substance or a suitable mixture of different liquids. For crystallizing 20DCM, the most appropriate solvent and/or solvent system is characterized by the following factors:

(1) low toxicity;
(2) low boiling point;
(3) significant dependence of solubility properties with regard to temperature (condition necessary for providing satisfactory crystallization yield); and
(4) relatively low cost.

Interestingly, hexane, so frequently used for crystallization purposes, was found less suitable as the sole solvent for crystallization of 20DCM. However, it was found that either ethyl formate, or a mixture of ethyl formate and hexane, was most useful for the crystallization of 20DCM. In particular, it was determined that a mixture of about 75% ethyl formate with about 25% hexane (by volume) performed well. The ethyl formate/hexane solvent mixture was also easy to remove by evaporation or other well known methods. In all cases the crystallization process occurred easily and efficiently; and the precipitated crystals were sufficiently large to assure their recovery by filtration or other means.

BRIEF DESCRIPTION OF THE DRAWINGS

FIG. 1 is an illustration of the three dimensional molecular structure for 20DCM as defined by the atomic positional parameters discovered and set forth herein;

DETAILED DESCRIPTION OF THE INVENTION

The present invention provides 1α-hydroxy-20-methyl-2-methylene-19,24,25,26,27-pentanorvitamin $D_3$ (20DCM) in crystalline form, a pharmacologically important compound, characterized by the formula I shown below:

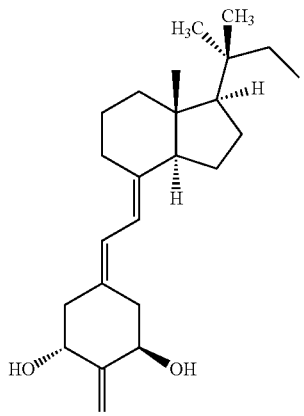

I

The present invention also provides a valuable method of purification of 20DCM. The purification technique involves obtaining the 20DCM product in crystalline form by utilizing a crystallization procedure wherein the 20DCM material to be purified is dissolved using as the solvent either ethyl formate as the sole solvent, or a mixture comprised of ethyl formate and hexane. Preferably the mixture comprises about 75% ethyl formate and about 25% hexane (by volume). Thereafter, the solvent can be removed by evaporation, with or without vacuum, or other means as is well known, or the resultant crystals may be filtered from the mother liquor. The technique can be used to purify a wide range of final products containing 20DCM obtained from any known synthesis thereof, and in varying concentrations, i.e. from microgram amounts to kilogram amounts. As is well known to those skilled in this art, the amount of solvent utilized should be minimized and/or adjusted according to the amount of 20DCM to be purified.

The usefulness and advantages of the present crystallization procedure is shown in the following specific Examples 1, 2 and 3. After crystallization, the precipitated material was observed under a microscope to confirm its crystalline form. Yields of crystals were relatively high and the obtained crystals showed a relatively sharp melting point of 140-145° C.

The described crystallization process of the synthetic 20DCM product represents a valuable purification method, which can remove most side products derived from the synthetic path. Such impurity is the result of the contamination of starting raw materials. The crystallization process occurred easily and efficiently; and the precipitated crystals were sufficiently large to assure their recovery by filtration, or other means.

Crystallization of 1α-hydroxy-20-methyl-2-methylene-19,24,25,26,27-pentanorvitamin $D_3$ (20DCM)

EXAMPLE 1

Crystallization from Ethyl Formate
1α-Hydroxy-20-methyl-2-methylene-19,24,25,26,27-pentanorvitamin $D_3$, 20DCM (15 mg), was dissolved in boiling ethyl formate (0.35 mL) and left at room temperature for about 1 hour, then it was kept in a refrigerator for about 18 hours. The precipitated crystals were filtered off, washed with a small volume of a cold (0° C.) ethyl formate and dried to give 9 mg (60%) of crystalline material.

EXAMPLE 2

Crystallization from Ethyl Formate/Hexane
1α-Hydroxy-20-methyl-2-methylene-19,24,25,26,27-pentanorvitamin $D_3$, 20DCM (15 mg), was dissolved in boiling ethyl formate (0.30 mL) and hexane (0.10 mL) was added. It was left at room temperature for about 1 hour, then it was kept in a refrigerator for about 18 hours. The precipitated crystals were filtered off, washed with a small volume of a cold (0° C.) ethyl formate/hexane (3:1) mixture and dried to give 10 mg (67%) of crystalline material.

EXAMPLE 3

Experimental

All crystal measurements were performed on a KM4CCD κ-axis diffractometer with graphite-monochromated MoK$_α$ radiation. The crystal was positioned at 62 mm from the CCD camera. 2186 frames were measured at 0.5° intervals with a counting time of 12 sec. The data were corrected for Lorentz and polarization effects. Empirical correction for absorption was applied[1] Data reduction and analysis were carried out with the Oxford Diffraction programs.[2]

The structure was solved by direct methods[3] and refined using SHELXL.[4] The refinement was based on $F^2$ for all reflections except those with very negative $F^2$. Weighted R factors wR and all goodness-of-fit S values are based on $F^2$. Conventional R factors are based on F with F set to zero for negative $F^2$. The $F_o^2 > 2σ(F_o^2)$ criterion was used only for calculating R factors and is not relevant to the choice of reflections for the refinement. The R factors based on $F^2$ are about twice as large as those based on F. All hydrogen atoms were located geometrically and their position and temperature factors were not refined. Scattering factors were taken from Tables 6.1.1.4 and 4.2.4.2 in Reference 5.

The three dimensional structure of 20DCM as defined by the following physical data and atomic positional parameters described and calculated herein is illustrated in FIG. 1.

TABLE 1

Crystal data and structure refinement for 20DCM.

| | |
|---|---|
| Identification code | 20dcm |
| Empirical formula | C24H38O2 |
| Formula weight | 358.54 |
| Temperature | 100(2) K |
| Wavelength | 0.71073 Å |
| Crystal system, space group | Orthorhombic, P2(1)2(1)2(1) |
| Unit cell dimensions: | |
| a = 6.6085(2) Å | alpha = 90 deg. |
| b = 15.8069(5) Å | beta = 90 deg. |
| c = 20.0641(7) Å | gamma = 90 deg. |
| Z, Calculated density | 4, 1.136 Mg/m^3 |
| Absorption coefficient | 0.070 mm−1 |
| F(000) | 792 |
| Crystal size | 0.70 × 0.40 × 0.35 mm |
| Theta range for data collection | 2.77 to 28.73 deg. |
| Limiting indices | −8 <= h <= 8, −20 <= k <= 21, −26 <= l <= 26 |
| Reflections collected/unique | 35848/3009 [R(int) = 0.0196] |
| Completeness to theta | = 28.00  99.7% |
| Absorption correction | Semi-empirical from equivalents |
| Max. and min. transmission | 0.98 and 0.96 |
| Refinement method | Full-matrix least-squares on $F^2$ |
| Data/restraints/parameters | 3009/13/261 |

TABLE 1-continued

Crystal data and structure refinement for 20DCM.

| | |
|---|---|
| Goodness-of-fit on $F^2$ | 1.084 |
| Final R indices [I > 2sigma(I)] | R1 = 0.0412, wR2 = 0.1103 |
| R indices (all data) | R1 = 0.0479, wR2 = 0.1136 |
| Largest diff. peak and hole | 0.217 and −0.256 e·Å$^{-3}$ |

TABLE 2

Atomic coordinates (×10$^4$) and equivalent isotropic displacement parameters (Å$^2$ × 10$^3$) for 20DCM. U(eq) is defined as one third of the trace of the orthogonalized Uij tensor.

| | x | y | z | U(eq) |
|---|---|---|---|---|
| O(1) | 8264(2) | −1494(1) | 9984(1) | 30(1) |
| O(2) | 2152(2) | −1902(1) | 10503(1) | 35(1) |
| C(1) | 6215(2) | −1295(1) | 10144(1) | 26(1) |
| C(2) | 5551(3) | −1666(1) | 10802(1) | 33(1) |
| C(2') | 6749(3) | −2110(2) | 11197(1) | 54(1) |
| C(3) | 3382(3) | −1462(1) | 10976(1) | 34(1) |
| C(4) | 3028(3) | −510(1) | 10959(1) | 39(1) |
| C(5) | 3801(3) | −104(1) | 10329(1) | 33(1) |
| C(6) | 2600(3) | 403(1) | 9970(1) | 37(1) |
| C(7) | 3083(3) | 859(1) | 9363(1) | 36(1) |
| C(8) | 1807(3) | 1350(1) | 9016(1) | 40(1) |
| C(9) | −379(3) | 1525(1) | 9198(1) | 58(1) |
| C(10) | 5961(3) | −331(1) | 10158(1) | 30(1) |
| C(11) | −833(4) | 2464(2) | 9220(1) | 67(1) |
| C(12) | −225(4) | 2915(2) | 8572(1) | 58(1) |
| C(13) | 2015(3) | 2770(1) | 8411(1) | 38(1) |
| C(14) | 2368(3) | 1800(1) | 8383(1) | 37(1) |
| C(15) | 4498(3) | 1722(1) | 8100(1) | 37(1) |
| C(16) | 4621(3) | 2444(1) | 7585(1) | 34(1) |
| C(17) | 2724(3) | 3012(1) | 7691(1) | 36(1) |
| C(18) | 3346(4) | 3155(1) | 8960(1) | 45(1) |
| C(20) | 3039(4) | 3933(1) | 7453(1) | 49(1) |
| C(20') | 4583(6) | 4425(2) | 7858(1) | 72(1) |
| C(21) | 3813(5) | 3899(2) | 6726(1) | 57(1) |
| C(22A) | 1282(8) | 4571(3) | 7457(3) | 53(1) |
| C(23A) | −387(7) | 4296(3) | 6993(3) | 71(2) |
| C(22B) | 749(8) | 4221(5) | 7469(4) | 49(2) |
| C(23B) | 348(13) | 5097(5) | 7183(4) | 71(3) |

TABLE 3

Bond lengths [Å] for 20DCM.

| | |
|---|---|
| O(1)—C(1) | 1.426(2) |
| O(1)—H(1O) | 0.8400 |
| O(2)—C(3) | 1.430(2) |
| O(2)—H(2O) | 0.8400 |
| C(1)—C(2) | 1.510(2) |
| C(1)—C(10) | 1.534(2) |
| C(1)—H(1) | 1.0000 |
| C(2)—C(2') | 1.321(3) |
| C(2)—C(3) | 1.510(3) |
| C(2')—H(2'A) | 0.9500 |
| C(2')—H(2'B) | 0.9500 |
| C(3)—C(4) | 1.524(3) |
| C(3)—H(3) | 1.0000 |
| C(4)—C(5) | 1.507(3) |
| C(4)—H(4A) | 0.9900 |
| C(4)—H(4B) | 0.9900 |
| C(5)—C(6) | 1.338(3) |
| C(5)—C(10) | 1.512(3) |
| C(6)—C(7) | 1.452(3) |
| C(6)—H(6) | 0.9500 |
| C(7)—C(8) | 1.340(3) |
| C(7)—H(7) | 0.9500 |
| C(8)—C(14) | 1.503(3) |
| C(8)—C(9) | 1.516(3) |
| C(9)—C(11) | 1.515(4) |
| C(9)—H(9A) | 0.9900 |
| C(9)—H(9B) | 0.9900 |

TABLE 3-continued

Bond lengths [Å] for 20DCM.

| | |
|---|---|
| C(10)—H(10A) | 0.9900 |
| C(10)—H(10B) | 0.9900 |
| C(11)—C(12) | 1.535(4) |
| C(11)—H(11A) | 0.9900 |
| C(11)—H(11B) | 0.9900 |
| C(12)—C(13) | 1.533(3) |
| C(12)—H(12A) | 0.9900 |
| C(12)—H(12B) | 0.9900 |
| C(13)—C(18) | 1.535(3) |
| C(13)—C(14) | 1.552(3) |
| C(13)—C(17) | 1.565(3) |
| C(14)—C(15) | 1.523(3) |
| C(14)—H(14) | 1.0000 |
| C(15)—C(16) | 1.541(3) |
| C(15)—H(15A) | 0.9900 |
| C(15)—H(15B) | 0.9900 |
| C(16)—C(17) | 1.556(3) |
| C(16)—H(16A) | 0.9900 |
| C(16)—H(16B) | 0.9900 |
| C(17)—C(20) | 1.547(3) |
| C(17)—H(17) | 1.0000 |
| C(18)—H(18A) | 0.9800 |
| C(18)—H(18B) | 0.9800 |
| C(18)—H(18C) | 0.9800 |
| C(20)—C(20') | 1.518(4) |
| C(20)—C(22A) | 1.537(4) |
| C(20)—C(21) | 1.547(3) |
| C(20)—C(22B) | 1.580(5) |
| C(20')—H(20D) | 0.9800 |
| C(20')—H(20E) | 0.9800 |
| C(20')—H(20F) | 0.9800 |
| C(21)—H(21A) | 0.9800 |
| C(21)—H(21B) | 0.9800 |
| C(21)—H(21C) | 0.9800 |
| C(22A)—C(23A) | 1.507(8) |
| C(22A)—H(22A) | 0.9900 |
| C(22A)—H(22B) | 0.9900 |
| C(23A)—H(23A) | 0.9800 |
| C(23A)—H(23B) | 0.9800 |
| C(23A)—H(23C) | 0.9800 |
| C(22B)—C(23B) | 1.523(9) |
| C(22B)—H(22C) | 0.9900 |
| C(22B)—H(22D) | 0.9900 |
| C(23B)—H(23D) | 0.9800 |
| C(23B)—H(23E) | 0.9800 |
| C(23B)—H(23F) | 0.9800 |

TABLE 4

Bond angles [°] for 20DCM.

| | |
|---|---|
| C(1)—O(1)—H(1O) | 109.5 |
| C(3)—O(2)—H(2O) | 109.5 |
| O(1)—C(1)—C(2) | 112.81(14) |
| O(1)—C(1)—C(10) | 109.03(14) |
| C(2)—C(1)—C(10) | 109.76(15) |
| O(1)—C(1)—H(1) | 108.4 |
| C(2)—C(1)—H(1) | 108.4 |
| C(10)—C(1)—H(1) | 108.4 |
| C(2')—C(2)—C(3) | 122.96(18) |
| C(2')—C(2)—C(1) | 123.77(18) |
| C(3)—C(2)—C(1) | 113.25(15) |
| C(2)—C(2')—H(2'A) | 120.0 |
| C(2)—C(2')—H(2'B) | 120.0 |
| H(2'A)—C(2')—H(2'B) | 120.0 |
| O(2)—C(3)—C(2) | 106.43(15) |
| O(2)—C(3)—C(4) | 112.18(16) |
| C(2)—C(3)—C(4) | 110.58(17) |
| O(2)—C(3)—H(3) | 109.2 |
| C(2)—C(3)—H(3) | 109.2 |
| C(4)—C(3)—H(3) | 109.2 |
| C(5)—C(4)—C(3) | 112.82(16) |
| C(5)—C(4)—H(4A) | 109.0 |
| C(3)—C(4)—H(4A) | 109.0 |
| C(5)—C(4)—H(4B) | 109.0 |

TABLE 4-continued

Bond angles [°] for 20DCM.

| Bond | Angle |
|---|---|
| C(3)—C(4)—H(4B) | 109.0 |
| H(4A)—C(4)—H(4B) | 107.8 |
| C(6)—C(5)—C(4) | 120.34(18) |
| C(6)—C(5)—C(10) | 125.47(18) |
| C(4)—C(5)—C(10) | 114.19(18) |
| C(5)—C(6)—C(7) | 128.22(18) |
| C(5)—C(6)—H(6) | 115.9 |
| C(7)—C(6)—H(6) | 115.9 |
| C(8)—C(7)—C(6) | 125.78(18) |
| C(8)—C(7)—H(7) | 117.1 |
| C(6)—C(7)—H(7) | 117.1 |
| C(7)—C(8)—C(14) | 123.88(17) |
| C(7)—C(8)—C(9) | 125.5(2) |
| C(14)—C(8)—C(9) | 110.64(19) |
| C(11)—C(9)—C(8) | 112.0(2) |
| C(11)—C(9)—H(9A) | 109.2 |
| C(8)—C(9)—H(9A) | 109.2 |
| C(11)—C(9)—H(9B) | 109.2 |
| C(8)—C(9)—H(9B) | 109.2 |
| H(9A)—C(9)—H(9B) | 107.9 |
| C(5)—C(10)—C(1) | 110.07(15) |
| C(5)—C(10)—H(10A) | 109.6 |
| C(1)—C(10)—H(10A) | 109.6 |
| C(5)—C(10)—H(10B) | 109.6 |
| C(1)—C(10)—H(10B) | 109.6 |
| H(10A)—C(10)—H(10B) | 108.2 |
| C(9)—C(11)—C(12) | 112.3(2) |
| C(9)—C(11)—H(11A) | 109.1 |
| C(12)—C(11)—H(11A) | 109.1 |
| C(9)—C(11)—H(11B) | 109.1 |
| C(12)—C(11)—H(11B) | 109.1 |
| H(11A)—C(11)—H(11B) | 107.9 |
| C(13)—C(12)—C(11) | 111.20(18) |
| C(13)—C(12)—H(12A) | 109.4 |
| C(11)—C(12)—H(12A) | 109.4 |
| C(13)—C(12)—H(12B) | 109.4 |
| C(11)—C(12)—H(12B) | 109.4 |
| H(12A)—C(12)—H(12B) | 108.0 |
| C(12)—C(13)—C(18) | 110.03(17) |
| C(12)—C(13)—C(14) | 107.5(2) |
| C(18)—C(13)—C(14) | 109.37(15) |
| C(12)—C(13)—C(17) | 116.55(16) |
| C(18)—C(13)—C(17) | 113.17(19) |
| C(14)—C(13)—C(17) | 99.38(15) |
| C(8)—C(14)—C(15) | 120.36(17) |
| C(8)—C(14)—C(13) | 113.59(16) |
| C(15)—C(14)—C(13) | 103.42(17) |
| C(8)—C(14)—H(14) | 106.2 |
| C(15)—C(14)—H(14) | 106.2 |
| C(13)—C(14)—H(14) | 106.2 |
| C(14)—C(15)—C(16) | 103.82(16) |
| C(14)—C(15)—H(15A) | 111.0 |
| C(16)—C(15)—H(15A) | 111.0 |
| C(14)—C(15)—H(15B) | 111.0 |
| C(16)—C(15)—H(15B) | 111.0 |
| H(15A)—C(15)—H(15B) | 109.0 |
| C(15)—C(16)—C(17) | 107.05(16) |
| C(15)—C(16)—H(16A) | 110.3 |
| C(17)—C(16)—H(16A) | 110.3 |
| C(15)—C(16)—H(16B) | 110.3 |
| C(17)—C(16)—H(16B) | 110.3 |
| H(16A)—C(16)—H(16B) | 108.6 |
| C(20)—C(17)—C(16) | 113.09(18) |
| C(20)—C(17)—C(13) | 123.75(16) |
| C(16)—C(17)—C(13) | 103.07(15) |
| C(20)—C(17)—H(17) | 105.1 |
| C(16)—C(17)—H(17) | 105.1 |
| C(13)—C(17)—H(17) | 105.1 |
| C(13)—C(18)—H(18A) | 109.5 |
| C(13)—C(18)—H(18B) | 109.5 |
| H(18A)—C(18)—H(18B) | 109.5 |
| C(13)—C(18)—H(18C) | 109.5 |
| H(18A)—C(18)—H(18C) | 109.5 |
| H(18B)—C(18)—H(18C) | 109.5 |
| C(20')—C(20)—C(22A) | 99.7(3) |
| C(20')—C(20)—C(17) | 114.01(17) |
| C(22A)—C(20)—C(17) | 120.9(3) |
| C(20')—C(20)—C(21) | 107.5(2) |
| C(22A)—C(20)—C(21) | 106.1(3) |
| C(17)—C(20)—C(21) | 107.65(17) |
| C(20')—C(20)—C(22B) | 119.1(4) |
| C(17)—C(20)—C(22B) | 97.8(3) |
| C(21)—C(20)—C(22B) | 110.2(3) |
| C(20)—C(20')—H(20D) | 109.5 |
| C(20)—C(20')—H(20E) | 109.5 |
| H(20D)—C(20')—H(20E) | 109.5 |
| C(20)—C(20')—H(20F) | 109.5 |
| H(20D)—C(20')—H(20F) | 109.5 |
| H(20E)—C(20')—H(20F) | 109.5 |
| C(20)—C(21)—H(21A) | 109.5 |
| C(20)—C(21)—H(21B) | 109.5 |
| H(21A)—C(21)—H(21B) | 109.5 |
| C(20)—C(21)—H(21C) | 109.5 |
| H(21A)—C(21)—H(21C) | 109.5 |
| H(21B)—C(21)—H(21C) | 109.5 |
| C(23A)—C(22A)—C(20) | 111.1(4) |
| C(23A)—C(22A)—H(22A) | 109.4 |
| C(20)—C(22A)—H(22A) | 109.4 |
| C(23A)—C(22A)—H(22B) | 109.4 |
| C(20)—C(22A)—H(22B) | 109.4 |
| H(22A)—C(22A)—H(22B) | 108.0 |
| C(23B)—C(22B)—C(20) | 114.9(6) |
| C(23B)—C(22B)—H(22C) | 108.5 |
| C(20)—C(22B)—H(22C) | 108.5 |
| C(23B)—C(22B)—H(22D) | 108.5 |
| C(20)—C(22B)—H(22D) | 108.5 |
| H(22C)—C(22B)—H(22D) | 107.5 |
| C(22B)—C(23B)—H(23D) | 109.5 |
| C(22B)—C(23B)—H(23E) | 109.5 |
| H(23D)—C(23B)—H(23E) | 109.5 |
| C(22B)—C(23B)—H(23F) | 109.5 |
| H(23D)—C(23B)—H(23F) | 109.5 |
| H(23E)—C(23B)—H(23F) | 109.5 |

Symmetry transformations used to generate equivalent atoms:

TABLE 5

Anisotropic displacement parameters ($Å^2 \times 10^3$) for 20DCM. The anisotropic displacement factor exponent takes the form: $-2\pi^2[h^2 a^{*2} U_{11} + \ldots + 2hka^*b^* U_{12}]$

| | U11 | U22 | U33 | U23 | U13 | U12 |
|---|---|---|---|---|---|---|
| O(1) | 17(1) | 39(1) | 35(1) | 7(1) | −2(1) | 1(1) |
| O(2) | 19(1) | 38(1) | 49(1) | 3(1) | −5(1) | 1(1) |
| C(1) | 16(1) | 36(1) | 25(1) | 5(1) | −2(1) | −2(1) |
| C(2) | 23(1) | 47(1) | 28(1) | 11(1) | −3(1) | −7(1) |
| C(2') | 29(1) | 91(2) | 41(1) | 35(1) | −4(1) | −6(1) |
| C(3) | 26(1) | 49(1) | 27(1) | 7(1) | 4(1) | −6(1) |
| C(4) | 37(1) | 49(1) | 32(1) | −7(1) | 11(1) | −7(1) |
| C(5) | 30(1) | 35(1) | 34(1) | −7(1) | 9(1) | −5(1) |
| C(6) | 27(1) | 43(1) | 42(1) | −7(1) | 10(1) | 3(1) |
| C(7) | 24(1) | 45(1) | 39(1) | −5(1) | 9(1) | 5(1) |
| C(8) | 24(1) | 59(1) | 36(1) | −5(1) | 6(1) | 9(1) |
| C(9) | 23(1) | 109(2) | 43(1) | 5(1) | 8(1) | 18(1) |
| C(10) | 24(1) | 35(1) | 30(1) | 0(1) | 3(1) | −4(1) |
| C(11) | 35(1) | 124(3) | 43(1) | 7(1) | 10(1) | 47(2) |
| C(12) | 37(1) | 102(2) | 36(1) | 1(1) | 1(1) | 43(1) |
| C(13) | 31(1) | 60(1) | 23(1) | −6(1) | −4(1) | 26(1) |
| C(14) | 22(1) | 58(1) | 30(1) | −8(1) | 2(1) | 10(1) |
| C(15) | 30(1) | 37(1) | 43(1) | −6(1) | 10(1) | 10(1) |
| C(16) | 29(1) | 42(1) | 30(1) | −7(1) | 2(1) | 6(1) |
| C(17) | 34(1) | 55(1) | 21(1) | −10(1) | −9(1) | 19(1) |
| C(18) | 59(1) | 52(1) | 23(1) | −7(1) | −10(1) | 30(1) |
| C(20) | 69(2) | 54(1) | 22(1) | −5(1) | −10(1) | 33(1) |
| C(20') | 135(3) | 43(1) | 37(1) | 3(1) | −22(2) | 4(2) |
| C(21) | 83(2) | 61(1) | 27(1) | −1(1) | −6(1) | 25(2) |
| C(22A) | 71(2) | 32(1) | 54(2) | 3(1) | 1(2) | 26(2) |
| C(23A) | 46(2) | 60(3) | 107(4) | 30(3) | −18(3) | 13(2) |
| C(22B) | 72(4) | 28(3) | 47(3) | 5(3) | 1(3) | 22(3) |
| C(23B) | 70(5) | 54(4) | 88(5) | 33(4) | 9(4) | 20(4) |

TABLE 6

Hydrogen coordinates (×10⁴) and isotropic displacement parameters ($Å^2 \times 10^3$) for 20DCM.

| | x | y | z | U(eq) |
|---|---|---|---|---|
| H(1O) | 8320 | −1979 | 9815 | 45 |
| H(2O) | 1091 | −1624 | 10431 | 53 |
| H(1) | 5325 | −1529 | 9785 | 31 |
| H(2'A) | 6255 | −2317 | 11610 | 64 |
| H(2'B) | 8104 | −2223 | 11066 | 64 |
| H(3) | 3079 | −1679 | 11433 | 41 |
| H(4A) | 1559 | −398 | 11000 | 47 |
| H(4B) | 3709 | −248 | 11346 | 47 |
| H(6) | 1262 | 474 | 10134 | 44 |
| H(7) | 4422 | 805 | 9196 | 43 |
| H(9A) | −1276 | 1251 | 8867 | 70 |
| H(9B) | −672 | 1274 | 9640 | 70 |
| H(10A) | 6888 | −84 | 10493 | 35 |
| H(10B) | 6316 | −92 | 9717 | 35 |
| H(11A) | −95 | 2722 | 9598 | 80 |
| H(11B) | −2299 | 2547 | 9297 | 80 |
| H(12A) | −1066 | 2702 | 8200 | 70 |
| H(12B) | −482 | 3530 | 8618 | 70 |
| H(14) | 1435 | 1579 | 8031 | 44 |
| H(15A) | 4697 | 1165 | 7883 | 44 |
| H(15B) | 5528 | 1795 | 8453 | 44 |
| H(16A) | 4632 | 2212 | 7127 | 40 |
| H(16B) | 5872 | 2778 | 7653 | 40 |
| H(17) | 1668 | 2773 | 7388 | 44 |
| H(18A) | 3262 | 2804 | 9362 | 67 |
| H(18B) | 2873 | 3728 | 9062 | 67 |
| H(18C) | 4753 | 3179 | 8806 | 67 |
| H(20D) | 4016 | 4558 | 8297 | 108 |
| H(20E) | 4922 | 4952 | 7625 | 108 |
| H(20F) | 5809 | 4083 | 7913 | 108 |
| H(21A) | 5186 | 3665 | 6719 | 86 |
| H(21B) | 3829 | 4472 | 6538 | 86 |
| H(21C) | 2915 | 3539 | 6460 | 86 |
| H(22A) | 741 | 4623 | 7915 | 63 |
| H(22B) | 1788 | 5133 | 7318 | 63 |
| H(23A) | −924 | 3749 | 7140 | 107 |
| H(23B) | 149 | 4242 | 6540 | 107 |
| H(23C) | −1472 | 4719 | 6998 | 107 |
| H(22C) | −64 | 3804 | 7216 | 59 |
| H(22D) | 274 | 4210 | 7937 | 59 |
| H(23D) | 595 | 5091 | 6701 | 106 |
| H(23E) | 1251 | 5509 | 7395 | 106 |
| H(23F) | −1062 | 5256 | 7268 | 106 |

TABLE 7

Torsion angles [deg] for 20DCM.

| | |
|---|---|
| O(1)—C(1)—C(2)—C(2') | 1.5(3) |
| C(10)—C(1)—C(2)—C(2') | −120.3(2) |
| O(1)—C(1)—C(2)—C(3) | −179.83(15) |
| C(10)—C(1)—C(2)—C(3) | 58.4(2) |
| C(2')—C(2)—C(3)—O(2) | −113.9(2) |
| C(1)—C(2)—C(3)—O(2) | 67.4(2) |
| C(2')—C(2)—C(3)—C(4) | 124.0(2) |
| C(1)—C(2)—C(3)—C(4) | −54.7(2) |
| O(2)—C(3)—C(4)—C(5) | −69.2(2) |
| C(2)—C(3)—C(4)—C(5) | 49.5(2) |
| C(3)—C(4)—C(5)—C(6) | 128.9(2) |
| C(3)—C(4)—C(5)—C(10) | −50.6(2) |
| C(4)—C(5)—C(6)—C(7) | 178.79(18) |
| C(10)—C(5)—C(6)—C(7) | −1.8(3) |
| C(5)—C(6)—C(7)—C(8) | 178.8(2) |
| C(6)—C(7)—C(8)—C(14) | −179.09(19) |
| C(6)—C(7)—C(8)—C(9) | 0.6(4) |
| C(7)—C(8)—C(9)—C(11) | 127.4(3) |
| C(14)—C(8)—C(9)—C(11) | −52.9(3) |
| C(6)—C(5)—C(10)—C(1) | −126.2(2) |
| C(4)—C(5)—C(10)—C(1) | 53.3(2) |
| O(1)—C(1)—C(10)—C(5) | −179.82(14) |
| C(2)—C(1)—C(10)—C(5) | −55.79(19) |
| C(8)—C(9)—C(11)—C(12) | 53.4(3) |

TABLE 7-continued

Torsion angles [deg] for 20DCM.

| | |
|---|---|
| C(9)—C(11)—C(12)—C(13) | −56.1(3) |
| C(11)—C(12)—C(13)—C(18) | −63.1(3) |
| C(11)—C(12)—C(13)—C(14) | 56.0(3) |
| C(11)—C(12)—C(13)—C(17) | 166.4(2) |
| C(7)—C(8)—C(14)—C(15) | −0.5(3) |
| C(9)—C(8)—C(14)—C(15) | 179.8(2) |
| C(7)—C(8)—C(14)—C(13) | −123.9(2) |
| C(9)—C(8)—C(14)—C(13) | 56.4(3) |
| C(12)—C(13)—C(14)—C(8) | −57.8(2) |
| C(18)—C(13)—C(14)—C(8) | 61.7(2) |
| C(17)—C(13)—C(14)—C(8) | −179.57(16) |
| C(12)—C(13)—C(14)—C(15) | 170.08(15) |
| C(18)—C(13)—C(14)—C(15) | −70.5(2) |
| C(17)—C(13)—C(14)—C(15) | 48.27(18) |
| C(8)—C(14)—C(15)—C(16) | −165.00(19) |
| C(13)—C(14)—C(15)—C(16) | −36.93(18) |
| C(14)—C(15)—C(16)—C(17) | 10.8(2) |
| C(15)—C(16)—C(17)—C(20) | 154.93(16) |
| C(15)—C(16)—C(17)—C(13) | 19.0(2) |
| C(12)—C(13)—C(17)—C(20) | 74.9(3) |
| C(18)—C(13)—C(17)—C(20) | −54.2(2) |
| C(14)—C(13)—C(17)—C(20) | −170.08(19) |
| C(12)—C(13)—C(17)—C(16) | −155.4(2) |
| C(18)—C(13)—C(17)—C(16) | 75.53(19) |
| C(14)—C(13)—C(17)—C(16) | −40.34(18) |
| C(16)—C(17)—C(20)—C(20') | −66.7(3) |
| C(13)—C(17)—C(20)—C(20') | 58.8(3) |
| C(16)—C(17)—C(20)—C(22A) | 174.4(3) |
| C(13)—C(17)—C(20)—C(22A) | −60.1(4) |
| C(16)—C(17)—C(20)—C(21) | 52.4(2) |
| C(13)—C(17)—C(20)—C(21) | 177.91(19) |
| C(16)—C(17)—C(20)—C(22B) | 166.6(3) |
| C(13)—C(17)—C(20)—C(22B) | −67.9(4) |
| C(20')—C(20)—C(22A)—C(23A) | 171.3(4) |
| C(17)—C(20)—C(22A)—C(23A) | −62.9(5) |
| C(21)—C(20)—C(22A)—C(23A) | 59.8(5) |
| C(22B)—C(20)—C(22A)—C(23A) | −43.7(9) |
| C(20')—C(20)—C(22B)—C(23B) | 63.7(7) |
| C(22A)—C(20)—C(22B)—C(23B) | 23.3(8) |
| C(17)—C(20)—C(22B)—C(23B) | −173.2(6) |
| C(21)—C(20)—C(22B)—C(23B) | −61.1(7) |

TABLE 8

Hydrogen bonds for 20DCM [Å and deg.]

| D-H...A | d(D-H) | d(H...A) | d(D...A) | <(DHA) |
|---|---|---|---|---|
| O(1)—H(1O)...O(2)#1 | 0.84 | 2.03 | 2.8149(19) | 154.8 |
| O(2)—H(2O)...O(1)#2 | 0.84 | 2.08 | 2.8466(17) | 150.9 |

Symmetry transformations used to generate equivalent atoms:

1 x+1/2,−y−1/2,−z+2  #2 x−1,y,z

REFERENCES

[1] CrysAlis RED, Oxford Diffraction Ltd.,Version 1.171.28cycle2 beta (release 25-10-2005 CrysAlis171.NET) (compiled Oct. 25, 2005, 08:50:05). Empirical absorption correction using spherical harmonics, implemented in SCALE3 ABSPACK scaling algorithm.

[2] CrysAlis CCD, Oxford Diffraction Ltd., Version 1.171.28cycle2 beta; CrysAlis RED, Oxford Diffraction Ltd.,Version 1.171.28cycle2 beta

[3] G. M. Sheldrick, Acta Crystallogr. 1990, A46, 467-473.

[4] G. M. Sheldrick, SHELXL93. *Program for the Refinement of Crystal Structures.*, Univ. of Göttingen, Germany.

[5] *International Tables for Crystallography*, Ed. A. J. C. Wilson, Kluwer:Dordrecht, 1992, Vol.C.

EXAMPLE 4

Synthesis of 20DCM

The preparation of 20DCM having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound IV to obtain compound I, i.e. 20DCM.

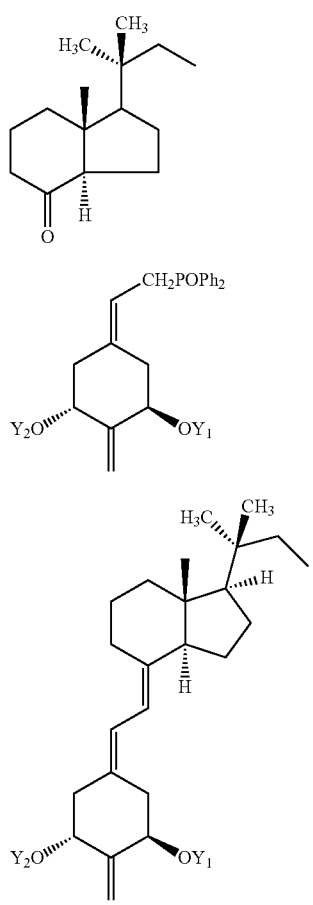

In phosphine oxide III, $Y_1$ and $Y_2$ are preferably hydroxy-protecting groups such as silyl protecting groups. The t-butyldimethylsilyl (TMDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al, U.S. Pat. No. 5,843,928 all of which are hereby incorporated by reference in their entirety and for all purposes as if fully set forth herein.

Phosphine oxide III is a convenient reagent that can be used to prepare a large number of 19-nor-vitamin D compounds and is prepared according to the procedures described by Sicinski et al., *J. Med. Chem.,* 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191 which are hereby incorporated by reference in their entirety as if fully set forth herein.

The overall process of the synthesis of compound I is illustrated and described more completely in U.S. Pat. No. 5,843,928 entitled "2-Alkylidene-19-Nor-Vitamin D Compounds" and in application Ser. No. 12/343,602 filed Dec. 24, 2008, entitled "2-Methylene-20-Methyl-19,24,25,26,27-Pentanor-Vitamin D Analogs" published as U.S. Publication No. US 2009/0170822 the specifications of which are specifically incorporated herein by reference.

We claim:

1. 1α-hydroxy-20-methyl-2-methylene-19,24,25,26,27-pentanorvitamin $D_3$ in crystalline form.

2. The crystalline form of 1α-hydroxy-20-methyl-2-methylene-19,24,25,26,27-pentanorvitamin $D_3$ having molecular packing arrangement defined by space group P2 and unit cell dimensions a=6.6 Å b=15.8 Å c=20.0 Å α=90°, β=90° and γ=90°.

3. A three dimensional structure for 1α-hydroxy-20-methyl-2-methylene-19,24,25,26,27-pentanorvitamin $D_3$ as defined by the molecular packing arrangement set forth in claim 2.

4. A method of purifying 1α-hydroxy-20-methyl-2-methylene-19,24,25,26,27-pentanorvitamin $D_3$, comprising the steps of:
    (a) preparing a solvent comprising ethyl formate;
    (b) dissolving a product containing 1α-hydroxy-20-methyl-2-methylene-19,24,25,26,27-pentanorvitamin $D_3$ to be purified in said solvent;
    (c) cooling said solvent and dissolved product below ambient temperature for a sufficient amount of time to form a precipitate of 1α-hydroxy-20-methyl-2-methylene-19,24,25,26,27-pentanorvitamin $D_3$ crystals; and
    (d) separating the 1α-hydroxy-20-methyl-2-methylene-19,24,25,26,27-pentanorvitamin$D_3$ crystals from the solvent.

5. The method of claim 4 including the further step of allowing said solvent and dissolved product to cool to ambient temperature prior to cooling below ambient temperature.

6. The method of claim 4 wherein said solvent comprises 100% ethyl formate, by volume.

7. The method of claim 4 wherein the step of separating comprises filtering the solvent and precipitate to obtain the crystals.

8. The method of claim 4 including a further step (e) comprising repeating steps (a) through (d) using the recovered crystals from step (d) as the product of step (b).

9. The method of claim 4 wherein said solvent comprises a mixture of ethyl formate and hexane.

10. The method of claim 9 wherein said mixture comprises about 75% ethyl formate and about 25% hexane, by volume.

11. A method of purifying 1α-hydroxy-20-methyl-2-methylene-19,24,25,26,27-pentanorvitamin $D_3$, comprising the steps of:
    (a) preparing a solvent comprising ethyl formate;
    (b) dissolving a product containing 1α-hydroxy-20-methyl-2-methylene-19,24,25,26,27-pentanorvitamin $D_3$ to be purified in said solvent;
    (c) cooling said solvent and dissolved product below ambient temperature for a sufficient amount of time to form a precipitate of 1α-hydroxy-20-methyl-2-methylene-19,24,25,26,27-pentanorvitamin $D_3$ crystals; and
    (d) recovering the 1α-hydroxy-20-methyl-2-methylene-19,24,25,26,27-pentanorvitamin $D_3$ crystals having a molecular packing arrangement defined by space group P2 and unit cell dimensions a=6.6 Å, b=15.8 Å, c=20.0 Å, α-90°, β=90° and γ=90°, or any other space group that yields substantially the same crystalline packing arrangement.

12. The method of claim 11 wherein said solvent and dissolved product is allowed to cool to ambient temperature prior to cooling below ambient temperature.

13. The method of claim 11 wherein said solvent comprises a mixture of ethyl formate and hexane.

14. The method of claim 13 wherein said mixture comprises about 75% ethyl formate and about 25% hexane, by volume.

15. The method of claim 11 wherein the step of recovering comprises filtering the solvent and precipitate to obtain the crystals.

16. The method of claim 11 including a further step (e) comprising repeating steps (a) through (d) using the recovered crystals from step (d) as the product of step (b).

* * * * *